United States Patent [19]
Mogg et al.

[11] 3,930,754
[45] Jan. 6, 1976

[54] PORTABLE WATER SAMPLING APPARATUS

[75] Inventors: Joe L. Mogg, Roseville; Rueben E. Paulson, Minneapolis, both of Minn.

[73] Assignee: Universal Oil Products Company, Des Plaines, Ill.

[22] Filed: Dec. 23, 1974

[21] Appl. No.: 535,906

[52] U.S. Cl. ............... 417/108; 166/264; 417/172; 73/155
[51] Int. Cl.² ..................... F01D 25/26; F03B 11/00; E21B 47/00
[58] Field of Search .......... 417/108, 109, 156, 172, 417/90; 73/155; 166/264

[56] References Cited
UNITED STATES PATENTS

| | | | |
|---|---|---|---|
| 640,463 | 1/1900 | Gildea | 417/172 |
| 3,722,589 | 3/1973 | Smith et al. | 166/264 |

FOREIGN PATENTS OR APPLICATIONS

| | | | |
|---|---|---|---|
| 60,708 | 3/1948 | Netherlands | 417/108 |

Primary Examiner—C. J. Husar
Assistant Examiner—Richard E. Gluck
Attorney, Agent, or Firm—James R. Hoatson, Jr.; Barry L. Clark; William H. Page, II

[57] ABSTRACT

Portable, self powered water pumping apparatus for use in sampling water in remotely located wells comprises a wheeled hose reel cart which supports a long length of plastic hose or tubing. The tubing has a small diameter length of inner tubing telescoped inside itself throughout most of its length. The inner tubing passes through the wall of the outer tubing near the upper end thereof and is connected to a pressurized cylinder of gas such as a standard 14 oz. propane gas cylinder. When the lower ends of the tubes are well submerged beneath the water level in a well, admission of gas to the inner tube at its upper end will force water up through an annular space between the tubes and out the upper end of the outer tube where it can be collected. A channeled plug at the bottom of the tubes prevents the tubes from collapsing, helps to keep them straight and together as they are lowered into the well and provides partial support for a weight hanging from the bottom of the tubes.

5 Claims, 3 Drawing Figures

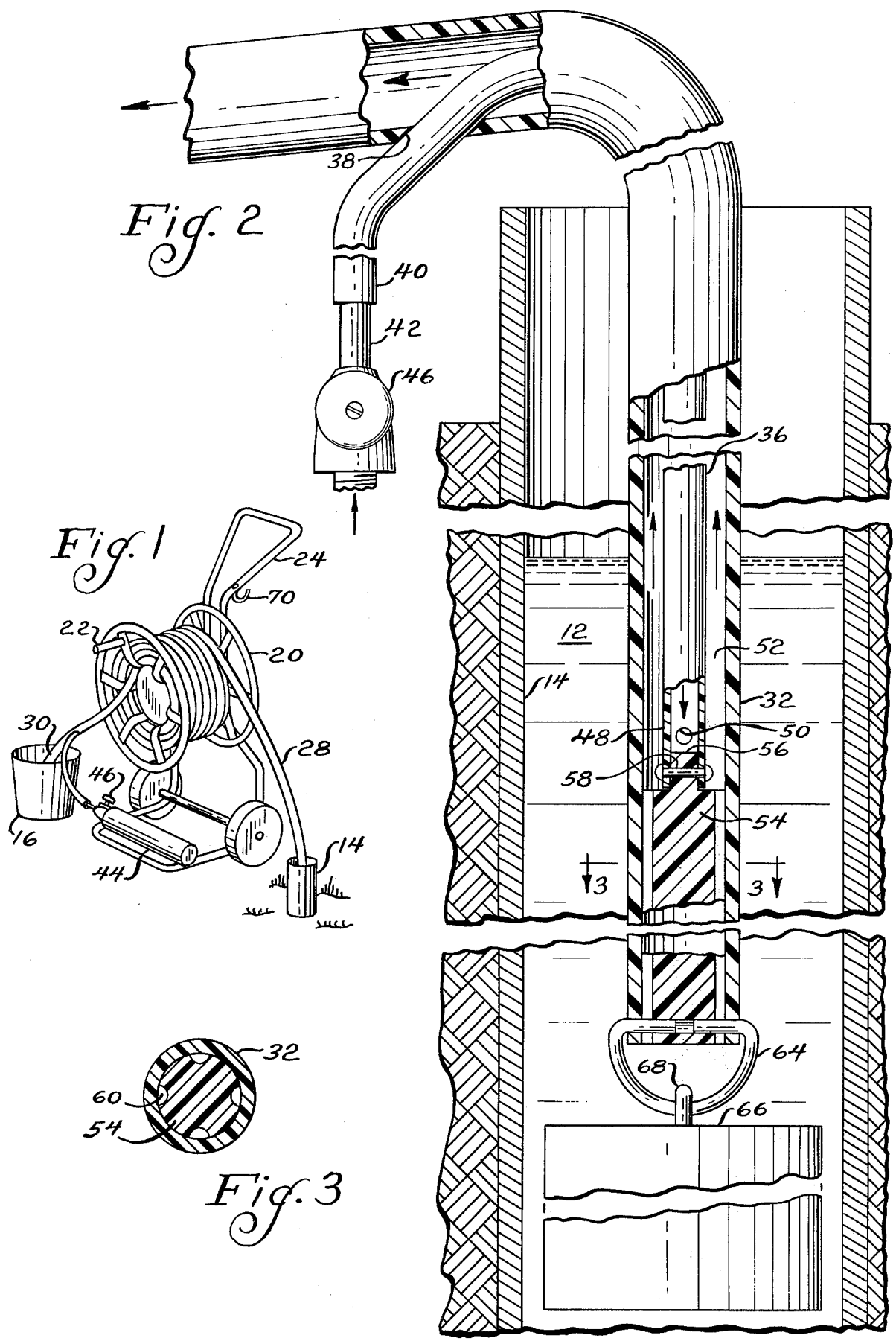

3,930,754

PORTABLE WATER SAMPLING APPARATUS

BACKGROUND OF THE INVENTION

The invention relates to sampling devices and particularly to devices for sampling water from remotely located wells such as non-active wells and observation wells as well as from new wells. It is common to place small diameter observation wells of about 2 or 3 inch diameter in a uniform pattern around much larger diameter water producing wells and in the same aquifer. By analyzing the drawdown of the observation wells in response to a drawdown of the pumping well, the permeability and transmissibility of the aquifer as well as its coefficient of storage, can be calculated. It is also important to sample the water in the observation wells to detect possible or potential contamination of the pumped well. Observation wells are also used in connection with injection wells wherein dangerous polluting liquids such as acids are injected into the earth to dispose of them. By taking periodic samples from observation wells in the vicinity of the injection well it is possible to determine if the pollutants are being contained as desired or whether they are spreading to a degree where they could contaminate water wells in the general area.

As a rule, the small observation wells or other wells which one might wish water samples from are situated in relatively remote locations which are inaccessible to sources of power for pumping up water samples. It would be desirable to have a low cost, self-powered, light weight piece of sampling equipment which could be easily carried to the job site in a utility vehicle rather than have to bring in heavy air compressors, generators or other bulky, expensive equipment for powering an air lift or other form of pump. It is among the objects of the present invention to provide such a piece of sampling equipment.

SUMMARY OF THE INVENTION

The invention basically comprises a pair of long concentric flexible plastic tubes which are wound around a reel which is mounted for rotation on a mobile cart which can be easily manually moved to the site of the well to be sampled. The inner tubing, which may, for example, have inner and outer diameters of 0.12 inch and 0.17 inch, respectively, is passed through a hole bored in the side of the larger tubing about one or two feet from one end thereof. The outer tubing, which may, for example, have inner and outer diameters of 0.375 inch and 0.500 inch, respectively, cooperates with the inner tube to form a cylindrical annular space having a radial thickness of about 0.10 inch. The outer tubing is wound on the reel so that the upper end thereof which has the inner tubing projecting from its side is positioned so as to project through the side of the reel a sufficient distance from the reel hub to permit the outer end of the outer tube to discharge pumped water into a container. The projecting portion of the inner tubing projects sufficiently far from the reel hub and outer tubing to facilitate the connection thereof to a gas cylinder and valve such as the universally available type used with a propane blow torch or a camp stove. The major portion of the tubing is wound about the reel for convenience in transporting it to a well and to simplify the lowering of the free end thereof into the well. Since the tubing assumes a degree of curvature when it is wound on the reel, a heavy weight is hung from its free end to help straighten out the tubing and facilitate its insertion into a well casing. An elongated channeled plug is placed inside the outer tube at its lower end to stiffen it and protect it. The plug also is attached to the inner tube and serves to maintain the annular spacing between the tubes, hold the free ends of the two tubes in a fixed relationship, and provide a rigid support for the heavy weight which might weigh 6 or 8 pounds, for example.

BRIEF DESCRIPTION OF THE DRAWINGS

FIG. 1 is a perspective view showing the water sampling apparatus in operation;
FIG. 2 is a partially sectioned, fragmentary view of the gas and water carrying sampling tubes and their relation to a well casing; and
FIG. 3 is a cross-sectional view taken on line 3—3 of FIG. 2.

DESCRIPTION OF THE PREFERRED EMBODIMENT

The portable water sampling apparatus is adapted to draw a sample of water 12 from within the well casing 14 and deliver it to a sample container 16. The sampling apparatus includes a hose reel 20 adapted to be rotated by a handle 22. The reel 20 is mounted for rotation on mobile cart 24 which has wheels to facilitate its movement over rough terrain. Wound about the reel 20 is a long length of outer tubing 28 which may be formed of polyethylene or other suitable material. The outer tube 28 has an upper end portion 30 from which water samples may be dispersed to a sample container 16, and a lower end portion 32 which is submerged beneath the level of water 12 in the well casing 14. Enclosed within the outer tube 28 for the major portion of its length is a smaller diameter inner tube 36 which may also be made of polyethylene or other suitable material. The inner tube 36 preferably extends through an opening 38 in the side wall of upper portion 30 of tube 28 but could also exit from tube 28 through the end thereof or through an appropriate tube fitting. The upper end 40 of the inner tube 36 is preferably pressed over a nozzle 42 on a gas cylinder 44 having a gas valve 46. Although the cylinder 44 could contain air, nitrogen or other low cost gas, it is generally more convenient to utilize small disposable cylinders of butane or propane gas which are readily available for use in blow torches and camp stoves. The lower end 48 of the inner tube 36 has openings 50 which communicate with the annular space 52 which is defined by the fact that the outer diameter of the inner tube 36 is less than the inner diameter of the outer tube 28.

A plug member 54 made of plastic or other suitable material and having a diameter for most of its length approximately equal to the inner diameter of the outer tubing 28 has a reduced neck portion 56 which engages the inside wall of inner tubing end portion 48 and is held thereto by a rivet 58 and, if desired, an appropriate cement. The plug 54 includes a plurality of longitudinal grooves 60 around its periphery which permit free flow of water 12 from the inside of the casing 14 to the annular space 52 between the two tubes. The plug 54 may be anchored to the outer tube 28 by means of cement and is additionally held by a formed wire member 64 which locks the tube 28 and plug 54 together and serves as a carrier ring for a heavy weight such as a lead weight member 66 which has a bail engaged by the holder 64. To prevent distortion of the tubing while it is being transported, the heavy weight 66 is preferably hooked onto a hook member 70 on the handle 22 of the mobile cart 24.

In operation, the weight 66 and the tubing 28 and 36 attached to it are lowered into the well casing 14 a sufficient distance to permit air lift pumping. With this type of pumping the minimum operating submergence is approximately 30 percent of the depth of the water inlet. In other words, approximately 30 percent of the length of the tube which is down the hole must be submerged. Assuming the gas exit openings 50 are sufficiently submerged to permit pumping to take place, the valve 46 on the gas cylinder 44 is opened to permit gas to pass down through the inner tube 36 and out the openings 50 where it will force the water in the annular space 52 upwardly through the space between the tubes and out the end 30 of the tube 28 into the container 16. If the openings 50 are not sufficiently submerged, no water will be pumped but gas will come to the surface. If the gas is butane or propane it will of course have an odor which may be detected so that the operator will know that the intake openings 50 are not sufficiently submerged. Commercially available propane cylinders generally have a pressure of 120 to 140 psi when new and warm which is generally sufficient to lift several gallons of water. For example, in one test where the ambient temperature was 75°F, the static water level was 76 feet and the sample intake was at 109 feet a single 14 ounce propane cylinder was able to lift a total of 8.6 gallons of water before its contents were exhausted. Since the gas cylinder must have a substantial pressure in order to pump water it is possible that a particular gas cylinder will still have a substantial charge remaining for blow torch or other use if the valve 46 is turned off as soon as the pumping rate decreases substantially. Since the gas cylinder 44 will exert a higher pressure when warm than when cold it is good practice in cold weather to keep the cylinder at room temperature until just before use.

We claim as our invention:

1. A portable water pumping apparatus for sampling water from a well comprising: a storage reel having a hub and side flanges and storing a pair of elongated, flexible, telescopically positioned, radially spaced inner and outer tubing members and for supporting the upper end portion of each of said tubing members; handle means on said storage reel for reeling and unreeling the lower end portion of said tubing members into a well; a cylinder of pressurized gas and complementary means on said cylinder and on the upper end portion of the inner tubing member for attaching said cylinder to the upper end of said inner tubing member, valve means for controlling the flow of gas from said cylinder into said inner tubing member; weight means attached to said outer tubing member at its lower end portion; the lower end portions of the inner and outer tubing member communicating with each other, means communicating the space between the inner and outer tubing members with water to be pumped; and discharge opening means at the upper end of the outer tubing member for discharging water forced up through the space between the inner and outer tubing members by gas passing down through the lower end portion of said inner tubing member from said cylinder when the lower end portion of each tubing member is submerged beneath the water in a well.

2. The water pumping apparatus of claim 1 wherein the upper end of said inner tubing member passes through the wall of said outer tubing member at a location spaced from the end thereof.

3. The water pumping apparatus of claim 1 wherein a plug member is fastened to the lower ends of said inner and outer tubing members to prevent relative movement between said tubing members and to maintain radial spacing between them.

4. The water pumping apparatus of claim 3 wherein the means communicating the space between the inner and outer tubing members with water to be pumped comprises longitudinal grooves in the peripheral surface of said plug member.

5. The water pumping apparatus of claim 4 wherein said weight means is attached to said outer tubing member by a fastener which passes through the wall of said tubing and engages the walls of aperture means in said plug.

* * * * *